United States Patent [19]

Preiss et al.

[11] Patent Number: 4,998,977
[45] Date of Patent: Mar. 12, 1991

[54] PUNCTURE SET FOR MEDICAL USE

[76] Inventors: Dieter Preiss, Schmidhofener Str. 22, Heitersheim-Gallenweiler, Fed. Rep. of Germany, 7843; Harald Wilke, Zur Schnapphahner Dell 5, St. Ingbert, Fed. Rep. of Germany, 6670

[21] Appl. No.: 94,780

[22] Filed: Sep. 10, 1987

[30] Foreign Application Priority Data

Mar. 2, 1987 [DE] Fed. Rep. of Germany ....... 3706625

[51] Int. Cl.⁵ .............................................. A61B 5/02
[52] U.S. Cl. ..................................... 128/673; 604/164
[58] Field of Search .................... 128/672.3, 675, 748, 128/344, 772, 656.8; 604/158-163, 167, 169

[56] References Cited

U.S. PATENT DOCUMENTS

| | | | |
|---|---|---|---|
| 3,081,770 | 3/1963 | Hunter | 128/748 X |
| 3,651,807 | 3/1972 | Huggins | 604/161 |
| 3,786,810 | 1/1974 | Pannier, Jr. et al. | 604/158 |
| 3,853,127 | 12/1974 | Spademan | 604/167 |
| 3,934,576 | 1/1976 | Daniellson | 604/169 X |
| 4,072,146 | 2/1978 | Howes | 128/674 |
| 4,177,809 | 12/1979 | Moorehead | 604/167 X |
| 4,192,319 | 3/1980 | Hargens et al. | 128/673 X |
| 4,406,656 | 9/1983 | Hattler et al. | 604/158 X |
| 4,468,224 | 8/1984 | Enzmann et al. | 604/164 X |
| 4,496,348 | 1/1985 | Genese et al. | 604/167 |
| 4,610,256 | 9/1986 | Wallace | 128/673 X |
| 4,641,654 | 2/1987 | Samson et al. | 128/344 |

FOREIGN PATENT DOCUMENTS 3109402 9/1982 Fed. Rep. of Germany ...... 128/672

Primary Examiner—Max Hindenburg
Attorney, Agent, or Firm—Fleit, Jacobson, Cohn, Price, Holman & Stern

[57] ABSTRACT

A puncture set and method to avoid blood loss when emplacing a catheter by a puncture set according to the Seldinger technique, and to enable blood pressure measurement during the puncturing, comprises a puncturing cannula (1) provided with a connecting piece (2) which has a lateral nipple (3) for connection to a pressure measurement line (4) of a pressure measuring device (5) and a pressure-tight cap (7) through which guide wire (8) is sealingly and slidably passed (to extend distally). The system is filled up to the pressure measurement transducer (5) with a physiological solution so that one obtains registration of the pressure even during the puncturing.

12 Claims, 3 Drawing Sheets

PUNCTURE SET FOR MEDICAL USE

PUNCTURE SET FOR MEDICAL USE

1. Technical Field

The invention relates to a puncture set for introducing a catheter into a blood vessel according to the Seldinger technique, wherein a metal puncturing-cannula is employed into which a wire is inserted, wherewith after the blood vessel (which may be, particularly, an artery) is successfully punctured the said wire is advanced into the blood vessel and, after withdrawal of the puncturing cannula, serves as a guide for the catheter which is to be inserted into the blood vessel. Arterial catheters are employed in anesthesia and intensive medicine, for pressure measurement or for repeated sampling of arterial blood. Also, such arterial catheters are used in [imaging-] radiology as a means of injecting a contrast medium.

2. Background Art

It is known to connect a pressure measurement device after inserting a catheter by the Seldinger technique, the device namely being connected [to the catheter] by means of a pressure measurement line which leads to a pressure measuring transducer with a visual display device. The display of the pressure curve enables the arterial pressure measurement to be read continuously. However, this technique has the disadvantage that when used under pathological circulation conditions the prior art technique with a puncture needle can be accompanied by substantial outflow and loss of blood.

The blood loss associated with this (prior art) technique is related to the speed at which the puncture cannula [(and connections thereto)] can be sealed.

STATEMENT OF THE INVENTION

The object of the present invention is to provide a puncture set for introducing a catheter, which is compatible with a pressure curve display device without giving rise to blood loss when employed with puncturing of the vessel by the Seldinger method, even when applied under extreme pathological conditions. This object is accomplished according to the invention by a connecting piece which is provided for the puncturing cannula, which cannula is provided with a grip piece, wherewith said connecting piece has a lateral nipple, and, at the proximal end, a pressure-tight cap through which the guide wire is slidably passed, under seal means. The pressure measurement line leading to the pressure measurement transducer can be connected to the lateral nipple, whereby following a successful puncturing (detected via the pressure curve display device) the guide wire, which has already been inserted into the puncture set, is present [i.e., is generally in place for adjustment whereby it can perform its function inside the blood vessel]. It is unnecessary to remove the pressure measurement line in order to advance the wire. By obviating such manipulations, one avoids any movements which might be attended by dislocation of the point of the cannula and resulting damage to the artery (e.g. by accidental puncturing of the far wall of the blood vessel), and one also avoids blood loss [which might occur during such manipulations even absent damage to the blood vessel]. Immediately following the puncturing, the wire can be advanced into the blood vessel. Subsequent procedure is according to the Seldinger method, with the puncture set being withdrawn along the guide wire, and the catheter [then] being inserted along said wire. If continuous blood pressure monitoring is indicated, the connecting piece with the pressure measurement line connected to it may remain connected to the catheter.

The invention also affords the unique advantage of allowing pressure measurement as the point of the cannula approaches the blood vessel. To achieve this, the entire system is filled, in advance of the puncturing, with a sterile physiological liquid which acts as a pressure transmitting medium and is in [(not necessarily wholly fluid)] communication with a pressure display device even prior to the time at which the point of the cannula penetrates the wall of the blood vessel.

The amplitudes in the pressure display indicate the approach of the point of the cannula to the vessel which is to be punctured. The pressure display also enables the operator to reliably determine whether the punctured vessel is a vein or an artery.

If it is desired to advance the guide wire into the puncturing cannula prior to the puncturing, with the aim of facilitating [i.e. speeding up] the procedure, one must have the interior bore of the puncturing cannula slightly larger than the cross sectional area of the guide wire, to allow pressure transmission [from the distal end of the cannula] to the interior of the connecting piece and thus to the pressure measurement transducer, prior to and/or after a successful puncturing.

According to a refinement of the invention, the pressure measurement transducer can be provided with an electronic pressure measurement sensor [i.e., with self-contained transducer] disposed on the end of a pressure measurement line which transmits the measurement voltage and is inserted into the connecting piece. In this way one eliminates a fluidic pressure measurement line which can detract from measurement accuracy. In the refinement the pressure measurement line is instead in the form of an electrical line, with the length of said line leading to the display device having no effect on measurement accuracy. Electronic pressure sensors mounted on the end of a measurement line similarly to thermocouples are per se known.

As described heretofore, after a successful puncturing the inventive puncture set must be separated [i.e., moved away] from the guide wire according to Seldinger, in order to advance the arterial catheter along the wire and into the blood vessel. According to another refinement of the invention, it is not necessary to accomplish this by withdrawing the puncture set along the length of the guide wire. Instead, a so-called separable cannula is provided which, along with its grip piece, can be broken apart longitudinally, via two mutually diametrically opposed notches and [with the aid of two] mutually diametrically opposed manipulating tabs formed on said grip piece, and can be removed. In connection with this [use of a separable cannula], the catheter which is to be inserted into the blood vessel will be [initially] disposed between the grip piece and the connecting piece. Then as soon as the fragments of the cannula [assembly] are removed, continuous blood pressure measurement can be instituted with minimal loss of blood.

Three exemplary embodiments of puncture sets according to the invention are illustrated in the drawings.

DETAILED DESCRIPTION OF THE INVENTION

Figure 1:
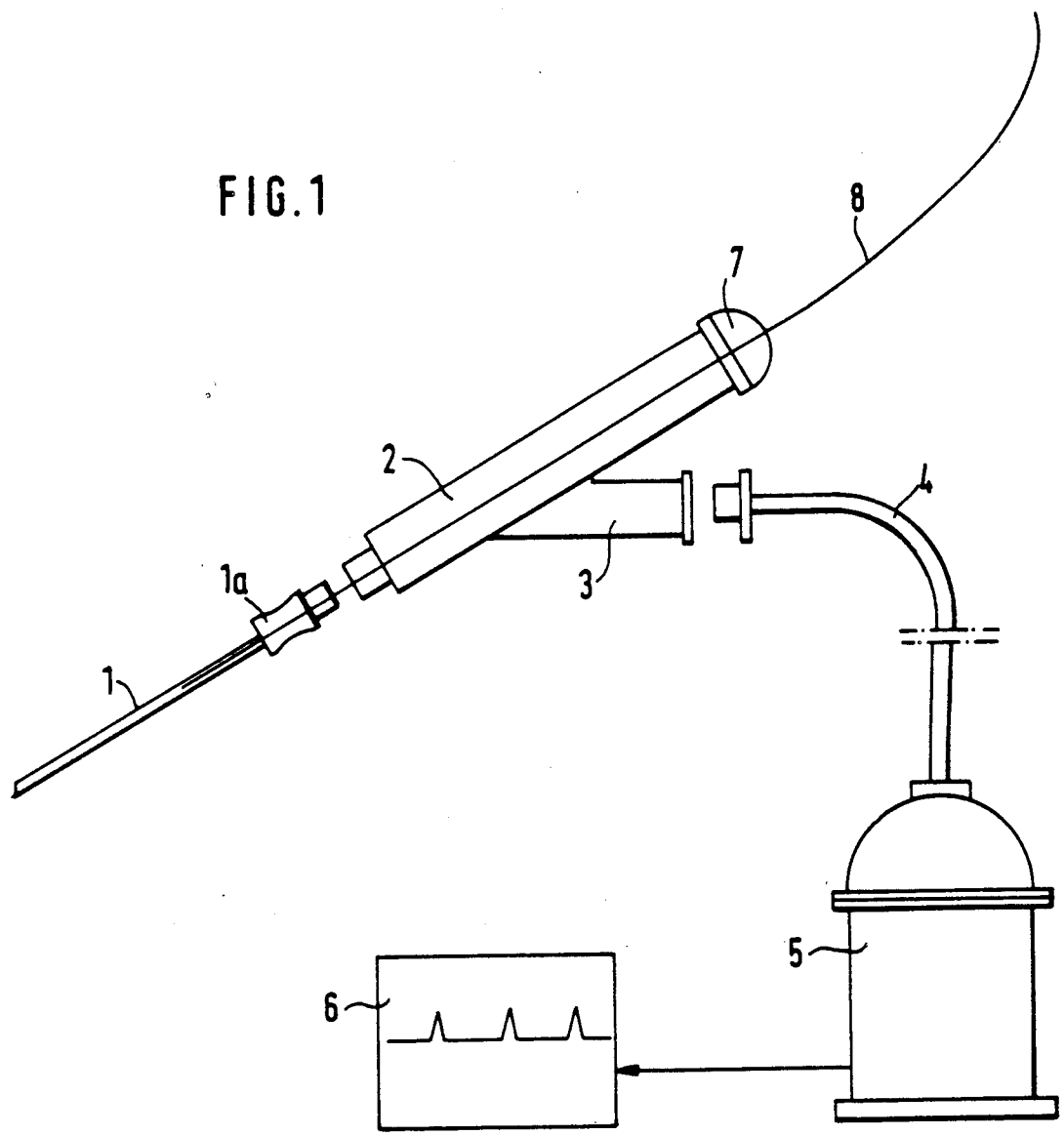
FIG. 1 shows a puncture set with a liquid-guiding pressure measurement line, in an exploded view.

According to FIG. 1, a puncturing cannula 1 bearing a grip piece 1a and a connecting piece 2 can be connected to a so-called Y-piece [i.e., Y-configuration] which is provided with a lateral nipple 3. A pressure measurement line 4 can be connected to nipple 3. Line 4 leads to a pressure measurement transducer 5 associated with a display device 6. The proximal end of the connecting piece 2 has a pressure-tight cap 7 which closes it off except for a calibrated opening through which a wire 8 has been inserted under seal means. The illustration of the exemplary embodiment shows how this wire is to extend into the interior bore of the puncturing cannula 1 prior to the initiation of the puncturing. Here the interior bore must be slightly larger [in cross sectional area] than the cross section of the wire, so that the blood pressure can be transmitted into the lateral nipple 3 and further to the pressure measurement transducer 5.

If the entire system (puncturing cannula 1, connecting piece 2, pressure measurement line 4, and pressure measurement transducer 5) is filled with a sterile physiological solution, a pressure curve can be registered on the display device 6 even during the insertion of the puncturing cannula.

[When] pressure curves appear on the display device indicating that the puncturing has been successful, the wire 8 is advanced into the blood vessel, and then the puncturing set (1, 2) is withdrawn over [and along] the wire (which is held fixed), whereby the arterial catheter can then be introduced via the wire. The pressure measurement can be continued if one connects the connecting piece 2 (which is still connected to the pressure measuring transducer 5) to the arterial catheter.

Figure 2:
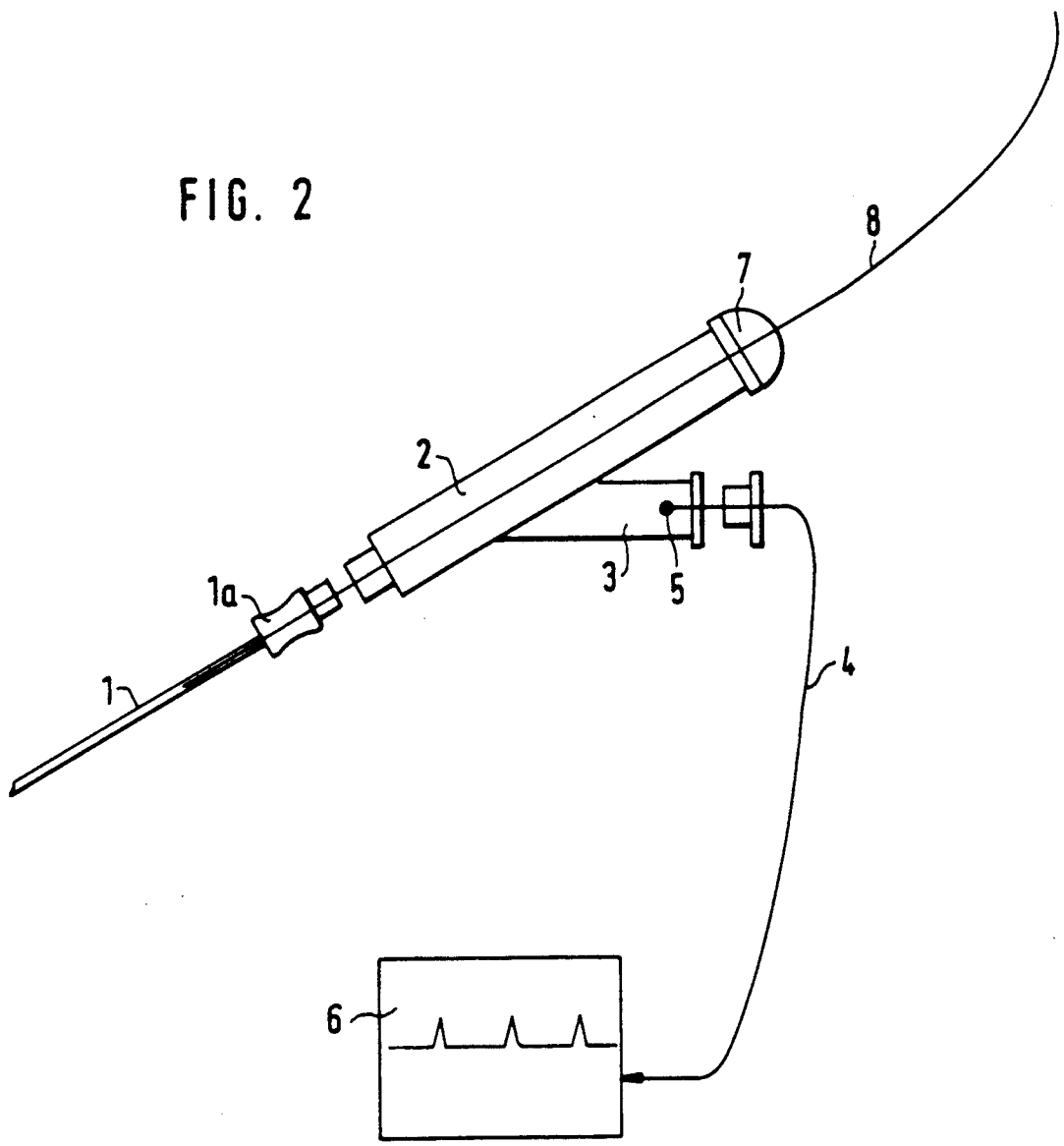
FIG. 2 is a view similar to FIG. 1, of a set with a pressure measurement line in the form of an electrical conductor.

FIG. 2 differs from FIG. 1 in that an electrical measuring line 4 is introduced into the lateral nipple 3 of the connecting piece 2, through a seal, which line 4 has a pressure measurement sensor 5 at its front end. The electrical pressure measurement line 4 which transmits the measurement voltage is directly connected to the display device 6, or is connected to it through a signal processing device and/or amplifier.

Figure 3:
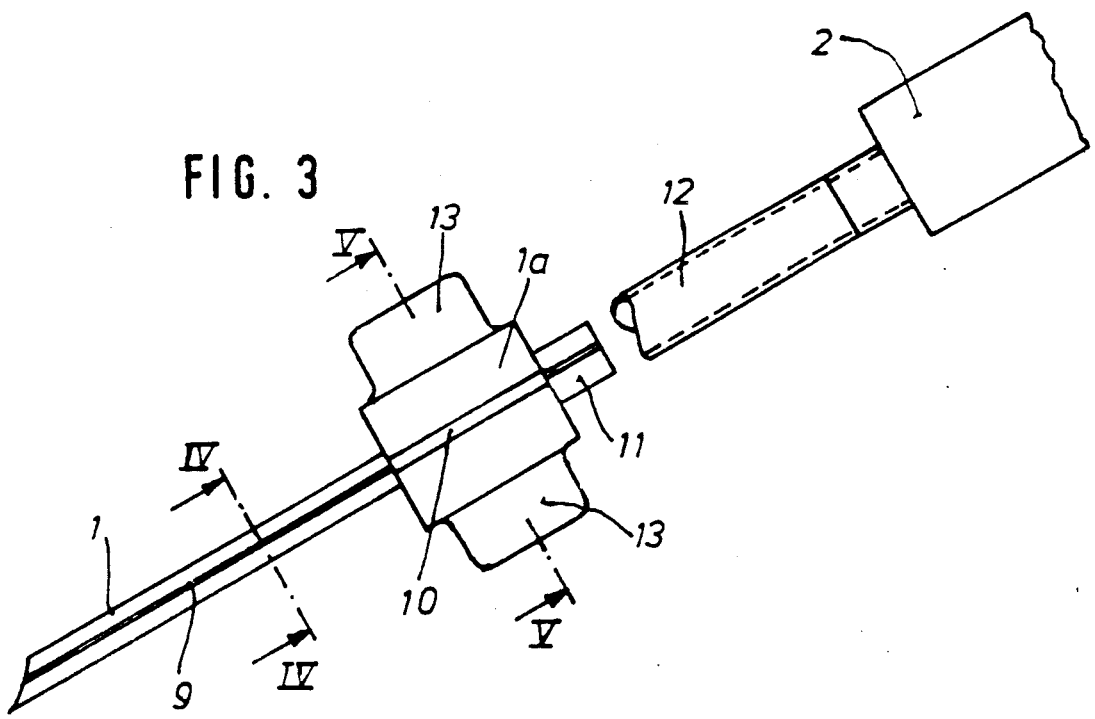
FIG. 3 is an enlarged partial view similar to FIGS. 1 and 2, with a separable cannula.
Figure 4:
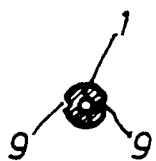
FIG. 4 is a cross section through line IV—IV of FIG. 3.
Figure 5:
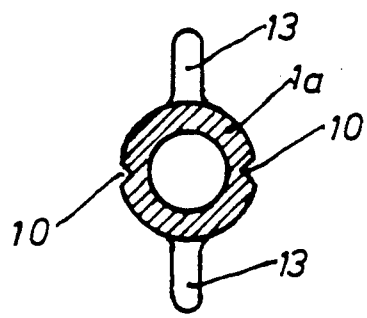
FIG. 5 is a cross section through line V—V of FIG. 3.

The metallic puncturing cannula 1 according to FIGS. 3 to 5 has two diametrically opposite, longitudinally extending notches 9 and there are two corresponding mutually diametrically opposite longitudinally extending notches 10 on the grip piece 1a. The nipple 11 formed on grip piece 1a, onto which nipple 11 the flexible plastic catheter 12 is pushed, has similar notches. Catheter 12 is rigidly connected to connecting piece 2. In a plane transverse to [the plane of] the slots (9, 10) there are two mutually diametrically opposite manipulating tabs 13 which are formed on the grip piece 1a.

After a successful puncture, the grip piece 1a is grasped by its manipulating tabs 13, and the assembly including the nipple 11 and the cannula 1 is broken apart [longitudinally] into two pieces, whereby the entire puncturing cannula [assembly] (1, 1a, 11) can be removed while the guide wire (not shown) remains inserted in the blood vessel. Immediately thereafter, the catheter 12 (shown shortened) can be inserted into the blood vessel. Because the catheter 12 is rigidly connected to the connecting piece 2, which was already prepared for pressure measurement at the time of the puncturing continuous blood pressure measurement can be initiated at once. The [guide] wire is then withdrawn from the puncture set.

We claim:

1. A puncture set for introducing a catheter into a blood vessel according to the Seldinger technique, comprising:
   a puncturing-cannula having a grip piece thereon;
   a connecting piece removably connected to said cannula;
   a hollow chamber in said connecting piece communicating with said cannula;
   sealing means at a proximal end of said connecting piece;
   a guide wire slidably insertable through said sealing means in sealing relation therewith and through said connecting piece, chamber and cannula;
   a lateral nipple on said connecting piece communicating with said hollow chamber in the interior of said connecting piece; and
   pressure measurement means connectable with said lateral nipple for communication with said hollow chamber for indicating successful puncture of said blood vessel by said puncturing-cannula.

2. A puncture set as claimed in claim 1 wherein:
   said puncturing cannula has an interior bore slightly larger in cross-sectional area than the cross-sectional area of said guide wire; and
   said hollow chamber is larger in cross-sectional area than said guide wire, so that pressure is reliably transmitted to said pressure measurement means after a successful puncturing when said guide wire is disposed in said puncturing cannula.

3. A puncture set as claimed in claim 1, wherein:
   said pressure measurement means comprises an electronic pressure measurement sensor disposed on the end of a pressure measurement line which conducts a measurement voltage and is inserted into said nipple.

4. A process for introducing a catheter into a blood vessel according to the Seldinger technique, comprising the steps of:
   coupling to a puncturing-cannula having a gripping piece, a connecting piece having a lateral nipple communicating with a hollow chamber in the interior of said connecting piece, and a proximal end, the connecting piece being adapted for straight guiding of a guide wire through said interior and into said puncturing-cannula;
   sealing said proximal end of said connecting piece with a sealing element;
   inserting and slidably guiding a guide wire through said sealing element in sealing relation therewith, said proximal end, said connecting piece and into said cannula;
   connecting means for measuring pressure within the interior of said connecting piece to said lateral nipple;

measuring pressure within the interior of said connecting piece before and during puncturing of blood vessel by said puncturing-cannula; and forcing said puncturing-cannula into the blood vessel to puncture the blood vessel.

5. The process as claimed in claim 4 and further comprising:

filling said cannula, connecting piece, lateral nipple and pressure measuring means with a physiological solution before penetration of the blood vessel by said puncturing-cannula.

6. The process as claimed in claim 5 and further comprising:

selecting the guide wire so that the cross-sectional area of the interior bore extending longitudinally through said puncturing-cannula is slightly larger than the cross-sectional area of the guide wire.

7. The process as claimed in claim 7 and further comprising:

selecting the guide wire so that the cross-sectional area of the interior bore extending longitudinally through said puncturing-cannula is slightly larger than the cross-sectional area of the guide wire.

8. A process for introducing a catheter into a blood vessel according to the Seldinger technique comprising the steps of:

coupling to a puncturing-cannula having a gripping piece, a connecting piece having a lateral nipple for communicating to the interior of said connecting piece, and a proximal end adapted for straight guiding of a guide wire through said interior and into said puncturing-cannula;

sealing said proximal end of said connecting piece with a sealing element through which a guide wire may be passed;

connecting means for measuring pressure within the interior of said connecting piece to said lateral nipple;

measuring pressure within the interior of said connecting piece before and during puncturing of the blood vessel by said puncturing-cannula; and forcing said puncturing-cannula into the blood vessel to puncture the blood vessel.

9. The process as claimed in claim 8 and further comprising:

selecting a guide wire whereby the cross-sectional area of the interior bore extending longitudinally through said puncturing-cannula is slightly larger than the cross-sectional area of the guide wire; and inserting the guide wire through the sealing element in sealing relation thereto and slidably guiding the guide wire through said connecting piece and into said cannula.

10. The process as claimed in claim 8 and further comprising:

filling said cannula, connecting piece, lateral nipple and pressure measuring means with a physiological solution before penetration of the blood vessel by said puncturing-cannula.

11. The process as claimed in claim 8 and further comprising:

selecting a guide wire whereby the cross-sectional area of the interior bore extending longitudinally through said puncturing-cannula is slightly larger than the cross-sectional area of the guide wire; and inserting the guide wire through the sealing element in sealing relation thereto and slidably guiding the guide wire through said connecting piece and into said cannula.

12. A puncture set for introducing a catheter into a blood vessel according to the Seldinger technique comprising:

a puncturing-cannula having a grip piece thereon;

a connecting piece removably connected to said cannula;

a hollow chamber in said connecting piece communicating with said cannula when connected thereto;

sealing means at a proximal end of said connecting piece;

a guide wire slidably insertable through said sealing means in sealing relation therewith and through said connecting piece, chamber and cannula;

a lateral nipple on said connecting piece communicating with said hollow chamber in the interior of said connecting piece;

a pressure measurement line connected to said lateral nipple;

a pressure measurement transducer coupled to said pressure measurement line; and a physiological solution filling said hollow chamber in said connecting piece, the pressure measurement line, and the pressure measurement transducer prior to the puncturing.

* * * * *